United States Patent
Haupert et al.

(10) Patent No.: US 6,580,948 B2
(45) Date of Patent: Jun. 17, 2003

(54) INTERFACE DEVICES FOR INSTRUMENTS IN COMMUNICATION WITH IMPLANTABLE MEDICAL DEVICES

(75) Inventors: David J. Haupert, Andover, MN (US); Charles R. Levan, Blaine, MN (US); Thomas J. Winkler, Isanti, MN (US); John M. Kruse, New Brighton, MN (US)

(73) Assignee: Medtronic, Inc., Minneapolis, MN (US)

( * ) Notice: Subject to any disclaimer, the term of this patent is extended or adjusted under 35 U.S.C. 154(b) by 33 days.

(21) Appl. No.: 09/838,696

(22) Filed: Apr. 19, 2001

(65) Prior Publication Data

US 2002/0007198 A1 Jan. 17, 2002

Related U.S. Application Data

(60) Provisional application No. 60/199,503, filed on Apr. 25, 2000.

(51) Int. Cl.$^7$ .................................................. A61N 1/37
(52) U.S. Cl. ............................ 607/60; 607/32; 607/30; 600/509
(58) Field of Search ........................... 607/27, 32, 37, 607/57, 60, 61, 5, 9, 30; 128/903; 600/509, 513

(56) References Cited

U.S. PATENT DOCUMENTS

| | | | |
|---|---|---|---|
| 4,374,382 A | 2/1983 | Markowitz | 340/870.01 |
| 4,593,284 A | 6/1986 | Clifford et al. | 340/870.18 |
| 4,677,986 A * | 7/1987 | DeCote, Jr. | 600/510 |
| 4,742,831 A | 5/1988 | Silvian | 128/710 |
| 4,751,726 A | 6/1988 | Hepp et al. | 379/93 |
| 4,858,617 A * | 8/1989 | Sanders | 600/509 |
| 4,987,897 A | 1/1991 | Funke | 128/419 PG |
| 5,127,401 A | 7/1992 | Grevious et al. | 128/419 PT |
| 5,168,871 A | 12/1992 | Grevious | 128/419 PT |
| 5,267,150 A | 11/1993 | Wilkinson | 364/413.02 |
| 5,345,362 A | 9/1994 | Winkler | 361/681 |
| 5,425,373 A | 6/1995 | Causey, III | 128/697 |
| 5,448,997 A | 9/1995 | Kruse et al. | 128/697 |
| 5,579,001 A * | 11/1996 | Dempsey et al. | 340/870.01 |
| 5,679,022 A | 10/1997 | Cappa et al. | 439/502 |

(List continued on next page.)

Primary Examiner—Carl Layno
(74) Attorney, Agent, or Firm—Girma Wolde-Michael

(57) ABSTRACT

External medical instruments that are in physical contact with a patient's body to communicate with or test the function of implantable medical devices (IMDs) implanted in the patient's body or to measure a physiologic condition of the patient's body and capable of communicating with other medical instruments or systems located at a distance from the patient, and, particularly, safety systems for protecting the patient from harm due to hazardous electrical signals or potentials. The external medical instrument operates pursuant to an instrument operating system that processes and generates electrical signals. A patient cable is coupled to a patient's body for transmitting electrical signals from the instrument operating system to the patient's body and for receiving electrical signals from the patient's body. A data cable extends to a remote instrument or a network, e.g., through a modem and Internet network connection, for communicating signals between the instrument operating system and the remote instrument or network. A first electrical isolation circuit between the instrument operating system and the data cable blocks conduction of hazardous electrical signals imposed upon the data cable from being conducted through the instrument operating system to the patient cable. A further electrical isolation circuit between the patient cable and the instrument operating system blocks conduction to the patient cable of hazardous signals conducted from the data cable through the instrument operating system.

18 Claims, 6 Drawing Sheets

U.S. PATENT DOCUMENTS

| | | |
|---|---|---|
| 5,683,432 A | 11/1997 | Goedeke et al. ............... 607/32 |
| 5,725,559 A | 3/1998 | Alt et al. ........................ 607/5 |
| 5,735,284 A * | 4/1998 | Tsoglin et al. ............... 600/508 |
| 5,749,908 A | 5/1998 | Snell ............................ 607/30 |
| 5,758,652 A | 6/1998 | Nikolic ........................ 128/673 |
| 5,782,892 A | 7/1998 | Castle et al. ................... 607/37 |
| 5,836,989 A | 11/1998 | Shelton ......................... 607/27 |
| 5,876,351 A * | 3/1999 | Rohde .......................... 600/523 |
| 5,931,861 A | 8/1999 | Werner et al. ............... 607/115 |
| 6,161,037 A * | 12/2000 | Cohen ......................... 600/513 |
| D438,204 S | 2/2001 | Winkler ........................ D14/356 |
| 6,375,614 B1 * | 4/2002 | Braun et al. ................. 600/300 |

* cited by examiner

INTERFACE DEVICES FOR INSTRUMENTS IN COMMUNICATION WITH IMPLANTABLE MEDICAL DEVICES

This application claims the benefits of the provisional application serial No. 60/199,503 filed Apr. 25, 2000.

BACKGROUND OF THE INVENTION

1. Field of the Invention

This invention relates to external medical instruments that are in physical contact with a patient's body to communicate with or test the function of implantable medical devices (IMDs) implanted in the patient's body or to provide a therapy or to measure a physiologic condition of the patient's body and capable of communicating with other medical instruments or systems located at a distance from the patient, and particularly to safety systems for protecting the patient from harm due to electrical potentials.

2. Description of the Prior Art

In the field of programmable IMDs, it has become common to provide an interactive, transceiver system for both remotely programming operating functions, modes and parameters of the implanted device, and for telemetering out data related thereto on command by RF telemetry to an external medical device, commonly denoted a "programmer". Such IMDs include cardiac pacemakers, cardiac and other physiologic monitors, implantable drug dispensers, nerve, muscle, and brain stimulators of various types, cochlear implants, blood pumps, cardiomyostimulators, and tachyarrhythmia-control devices, e.g., implantable cardioverter/defibrillators (ICDs) for delivery of staged therapies to the ventricles and/or the atria, etc., to treat tachyarhythmias.

At the present time, both analog and digital information or data is typically transmitted by uplink RF telemetry from such IMDs to the external programmer upon receipt of a downlink telemetry interrogation command from the external programmer. The analog information has typically included battery voltage, physiologic signal amplitudes sensed in real time from sensors or sense electrodes, e.g., sampled cardiac electrocardiogram or EGM amplitude values, and, in the case of implanted pacemaker and ICD IPGs, pacing pulse and/or cardioversion shock amplitude, energy, and pulse width and lead impedance. Digital information includes digitized operating data, e.g., markers signifying device operations and data typically stored in RAM or ROM and transmitted in response to an interrogation command from such IMDs. Such stored data includes historic statistics related to device performance, episodic physiologic data stored in response to detection of an episode of interest or delivery of a therapy, e.g., cardiac electrogram (EGM) segments, current programmed operating modes and parameter values, implant data, and patient and IMD identifier codes. Uplink telemetry is therefore employed to interrogate the IMD functions and memory and to confirm re-programming of operating modes and parameter values programmed in a downlink telemetry transmission.

Since the time that such telemetry systems first became available, IMDs have proliferated in types and successive models or generations of each type that have been steadily improved in longevity and designed with increased programmable functions and capabilities. At first, in some instances, a single external programmer was designed to function with a single type or family of IMDs that could not be used to program or interrogate other IMD types or families or new generations thereof. A new programmer would have to be provided to the physicians as successive programmable IMD models and IMD functions became clinically available. In some instances, this problem was perceived and dealt with by providing the capability of upgrading the programmer so that it could communicate with the newly available IMDs and at least confirm the identity of the IMD during a programming session for safety and record keeping reasons before proceeding to the programming and interrogation functions.

Medtronic, Inc. and other manufacturers developed microprocessor-based programmers that operated using software routines provided by dedicated, plug-in ROM modules or cartridges to enable the operation of the programming and interrogation telemetry with regard to specific model or series of models of IMDs. In such systems, the programmer is incapable of communicating with a given IMD model unless the appropriate plug-in module or cartridge is first installed. For example, for many years, particular Medtronic® MemoryMod® ROM cartridges were developed and supplied to enable the physician to upgrade the programmer to program and interrogate a specific set of new generation Medtronic® pacemaker implantable pulse generator models.

More sophisticated, computer based programmers have been developed that also can be upgraded, including, for example, the Medtronic® Model 9710 and 9760 programmers and the more recent Medtronic® Model 9766 and 9790 programmers which employ the Medtronic® Model 9765 programming head. It is possible to load updated software for programming new generation IMDs onto a hard disk drive from floppy disks or compact discs or through a modem and many of the other alternative ways that programs are added to personal computers, for example.

Telemetry sessions between an IMD and the external programmer are typically initiated and conducted in the manner described in commonly assigned, U.S. Pat. Nos. 5,168,871 and 5,683,432. Current telemetry systems are designed to provide two-way telemetry by RF signal transmission and linkage between an antenna coil contained in the IMD canister and an antenna coil or coils contained in the programming head of the external programmer. Typically, the programming head is placed against the patient's skin overlying the IMD, and a communications link is established as depicted and described in the above-referenced '871 patent by closure of a reed switch within the IMD by the magnetic field of a permanent magnet incorporated into the programming head. Uplink telemetry of analog and digital data of the IMD and downlink telemetry of programming and interrogation commands to the IMD is conducted in a telemetry session according to a telemetry format that is related to the particular IMD.

Programmers and IMDs have also been disclosed that transmit and receive programming instructions and data at high frequencies employing very small antennae and that eliminate the need for the closure of the reed switch by the external magnet during programming.

FIG. 1 is a simplified view of the typical bidirectional telemetry communication between a prior art external programmer 26 and an IMD comprising a cardiac pacemaker implantable pulse generator (IPG) 12 and an associated lead 14, for example, employing the programming head 20. The IPG 12 is implanted in the patient 10 beneath the patient's skin and typically oriented to the skin surface as is typical in the implantation of any programmable and interrogatable IMD. The IPG 12 is electrically coupled to the heart 18 of the patient 10 through pace/sense electrodes and lead conductor(s) of at least one cardiac pacing lead 14 in a manner known in the art. The IPG 12 contains an operating system that may employ a microcomputer or a digital state machine for timing sensing and pacing functions in accordance with a programmed operating mode. The IPG 12 also contains sense amplifiers for detecting cardiac signals, patient activity sensors or other physiologic sensors for sensing the need for cardiac output, and pulse generating output circuits for delivering pacing pulses under control of the operating system in a manner well known in the prior art. The operating system includes memory registers or RAM for storing a variety of programmed-in operating mode and parameter values that are used by the operating system. The memory registers or RAM may also be used for storing data compiled from sensed cardiac activity and/or relating to operating history for telemetry out on receipt of a retrieval or interrogation instruction. All of these functions and operations are well known in the art, and many are employed in other programmable, IMDs to store operating commands and data for controlling device operation and for later retrieval to diagnose device function or patient condition.

Programming commands or data are transmitted between an IPG telemetry antenna within IPG 12 and a programming head telemetry antenna within programming head 20 during a telemetry uplink transmission 28 or downlink transmission 30. In a telemetry uplink transmission 28, the programming head telemetry antenna operates as a telemetry receiver antenna, and the IPG telemetry antenna operates as a telemetry transmitter antenna. Conversely, in a telemetry downlink transmission 30, the programming head telemetry antenna operates as a telemetry transmitter antenna, and the IPG telemetry antenna operates as a telemetry receiver antenna.

INTERROGATE push-button 23 and PROGRAM push-button 25 and an LED display 22 are provided on the programming head 20 and are also electrically connected through electrical cable 24 to external programmer 26. The INTERROGATE and PROGRAM push-buttons 23 and 25 are provided to be selectively depressed by the medical care giver to start the telemetry uplink and downlink transmissions 28 and 30, respectively, as described in detail in the above-referenced '871 patent. The LED display 22 is also provided that is coupled to a sense circuit in programmer 26 described above and is illuminated during a telemetry uplink or downlink transmission 28 or 30 to alert the medical person that the transmission is taking place.

An ECG cable 60 is also provided extending from programmer 56 having a plurality of ECG skin electrodes that can be placed at specified points of the patient's torso and limbs. Graphics display screen 55 is used to display the patient related data and menu choices and data entry fields used during telemetry uplink and downlink transmissions 28 and 30. The user interacts with programmer 26 by touching stylus 56 against a selected location on screen 55 that displays the appropriate menu choices. Other components within the programmer console are described below with reference to FIG. 2.

The programmer 26 is typically employed during implantation of the IMD to program initial operating modes and parameter values and to obtain implant patient data for the patient's medical record. The programmer 26 is also employed from time to time during routine patient follow-up visits or when a clinical issue arises causing the patient to seek medical assistance in order to uplink telemeter patient data and IMD operating stored data to the programmer for analysis. In use, the attending medical care giver applies the ECG skin electrodes to the patient's body and/or holds programming head 20 against the patient's skin and over the IPG 12 to align the transceiver antennas in each as close together and as still as possible to ensure reliable telemetry transmission during the time that it takes to complete a telemetry uplink or downlink transmission 28 or 30.

A simplified block diagram of an exemplary prior art programmer 26 is set forth in FIG. 2 and is based upon the above-referenced Medtronic® Model 9760 programmer or preferably the Model 9790 programmer that is depicted and described in the above-referenced '432 patent. Programmer 26 is a personal computer type, microprocessor-based device incorporating a central processing unit 50, which may be, for example, an Intel 80386 or 80486 or Pentium microprocessor or the like. A system bus 51 interconnects CPU 50 with a hard disk drive 52 storing operational programs and data and with a graphics circuit 53 and an interface controller module 54. A floppy disk drive 36 (or a CD ROM drive) is also coupled to bus 51 and is accessible via a disk insertion slot (not shown) within the housing of the programmer 26. Programmer 26 further comprises an interface module 57, which includes digital circuit 58, non-isolated analog circuit 59, and isolated analog circuit 40. Digital circuit 58 enables interface module 57 to communicate with interface controller module 54.

An alphanumeric keyboard 45 for entering text or numbers and other symbols is optionally provided to allow the medical person to communicate with CPU 50 in the programmer 26. However, the primary user communication mode is through graphics display screen 55 of the well known "touch sensitive" type controlled by graphics circuit 53 and a stylus 56 coupled thereto. As noted above, graphics display screen 55 is used to display the patient related data and menu choices and data entry fields used during telemetry uplink and downlink transmissions 28 and 30, and stylus 56 is used to select appropriate menu choices.

Graphics display 55 also displays a variety of screens of telemetered out data or real time data. Programmer 26 is also provided with a strip chart printer 63 or the like coupled to interface controller module 54 so that a hard copy of a patient's ECG, atrial and/or ventricular electrogram (AEGM, VEGM), Marker Channel or of graphics displayed on the display 55 can be generated.

The transceiver circuitry 41 is connected to the interface module 57 of the external programmer 26 via conductors in an elongated electrical cable 24. During a telemetry uplink transmission 30, the telemetry receiver circuit in transceiver 41 is enabled. The telemetered out RF pulses of the uplink transmission 30 are detected, demodulated, decoded and applied to the digital circuit 58 to be digitized and recorded in RAM or in a hard or floppy disk or the like. The digitized data may be contemporaneously or later retrieved from memory and displayed on graphics display screen 55 or printed out for the attending medical personnel.

The analog and ventricular channel EGM signals from atrial and ventricular pace/sense electrodes may be digitized within IPG 12 and uplink telemetered to programmer 26 on receipt of a suitable INTERROGATE command. The uplink transmission 28 of the telemetered EGM signals are received in programming head 20 and provided to non-isolated analog circuit 59. Non-isolated analog circuit 59, in turn, convert the digitized EGM signals to analog EGM signals (as with a digital-to-analog converter, for example) and presents these signals on output lines designated in FIG. 2 as AEGM OUT and VEGM OUT. These output lines may then be applied to a separate strip-chart recorder or the like to provide a hard-copy printout of the AEGM or VEGM signals transmitted from IPG 12 for viewing by the physician The IPG 12 may also be capable of generating so-called marker codes indicative of different cardiac events that it detects. An IPG with Marker Channel capability is described, for example, in commonly assigned U.S. Pat. No. 4,374,382, incorporated by reference herein in its entirety. The markers provided by IPG 12 may be received by programming head 20 and presented on the MARKER CHANNEL output line from non-isolated analog circuit 59.

To initiate a telemetry uplink transmission 28, the telemetry transmitter in transceiver 41 is enabled in response to depression of the INTERROGATE push-button to generate an INTERROGATE RF pulse command that first initiates a downlink telemetry transmission 30 of a series of RF pulses. Each RF pulse of the instruction or command that is transmitted causes the IPG L-C tuned circuit to ring. The train of induced voltages is detected and decoded by the receiver circuit in the IPG transceiver. After the command or instruction is decoded, the stored data to be uplink transmitted is encoded into PPM modulated RF pulses in data frames. Methods and apparatus for formatting such uplink data frames for Medtronic® IPGs and other IMDs are set forth in detail in the above-referenced '404 patent. The transmitter circuit in the IPG transceiver applies voltage to the IPG RF antenna causing the L-C tuned circuit to ring and generate the uplink RF pulses which induce signals in the programming head telemetry antenna. The induced signals are detected in the telemetry receiver circuit in transceiver 41 and applied as a pulse train on cable 24 to interface module 57 where the frame of a series of such signals is decoded so that the data can be recorded or displayed as described above.

Some preliminary electrical tests are typically performed after an implantable cardioversion or defibrillation lead is implanted and before the lead is finally attached to the IMD IPG. For example, if the lead is a pacing lead that is to be connected to an implantable pacemaker IPG or ICD IPG, the lead is first implanted (e.g., transvenously) so that the distal electrode(s) is in electrical contact with cardiac tissue as shown in FIG. 1. Then, the proximal lead connector remaining outside the skin is temporarily connected to an appropriate external stimulator typically through an elongated surgical cable so that stimulation thresholds effective to capture the heart, sensing thresholds, and lead impedance data can be collected. The external instrument is referred to as a pacing system analyzer (PSA) when a pacing leads are tested or as a defibrillation system analyzer (DSA) when cardioversion/defibrillation leads are also tested as described in U.S. Pat. No. 5,679,022. Exemplary PSAs include the MEDTRONIC® Model No. 5311B PSA, the MEDTRONIC® Model 5410/S reusable surgical cable and the combination of the MEDTRONIC® Model 5411/S reusable adaptor and Model 5455/S disposable surgical cable. Such PSA models are stand-alone battery powered devices having integral operating controls and display.

A DSA is used to apply an appropriate signal (usually a low amplitude AC signal) to the shocking electrodes in order to induce fibrillation. Shocking pulses of varying energies are then applied to the cardiac tissue across the shocking electrodes in order to ascertain the defibrillation threshold, i.e., the amount of energy required in a defibrillation shock pulse in order to defibrillate the heart. The determined defibrillation threshold is then used to guide the initial setting of the defibrillation energy generated by the ICD IPG.

In use of a PSA, a series of stimulation pulses of varying energies, or other test signals (such as signals to measure the lead impedance) can be applied to the cardiac tissue through the lead in order to ascertain the capture threshold at which the cardiac muscle tissue contracts, or in order to determine other parameters associated with the lead. The results of such capture threshold testing, or other testing, advantageously provide an indication as to whether the distal electrode is making good contact with the cardiac tissue, as well as what the initial setting of the pacing pulse energy should be to reliably capture the heart.

FIG. 1 also illustrates a PSA 70 having a PSA cable 72 extending to connectors 74 and 76 adapted to be coupled to the proximal connector elements of a bipolar lead 14, for example, that would exit the skin incision that the lead 14 is introduced through prior to attachment to the IPG 12 and the subcutaneous implantation of IPG 12. In this particular instance, the PSA 70 is the MEDTRONIC® Model No. 8090 PSA that is built into a lid of a compartment of the Model 9790 programmer 26. Software to operate the Model 8090 PSA pulse generators, sense amplifiers and impedance measurement circuitry, to display menus for selection, the delivered pacing pulses and the test values and to print a record of the same is loaded into the programmer operating system.

In use, the clinician enters control values and commands for operating the Model 8090 PSA using the keyboard 45 and display 55. The Model 8090 PSA executes the commands under the control of the CPU 50 to deliver an impedance test pulse, for example, to measure voltage and current and to derive an impedance value. The derived value or other signal is then displayed on display 55, printed out by printer 43 and stored in memory with other patient data.

There is a risk of accidental injury to a patient whenever electrically powered medical equipment is coupled with the patient's body, and steps have been taken to minimize that risk using a conventional programmer 26 or PSA 70 or other ECG equipment. In FIG. 2, the programmer 26 includes a medical grade power supply 66 that powers the CPU 50, the other circuitry and the peripheral devices including the display 55 and printer 43 and is typically coupled to electrical mains. The power supply 66 is electrically isolated from the powered circuitry and components through a high voltage isolation transformer to prevent any mains current or voltage from being coupled to the ECG leads 60 or through the PSA 70 and the cable 72 to the implanted leads, e.g., lead 14.

In addition, an isolated analog circuit 40 in interface module 57 is provided to receive the external ECG signals via ECG cable 60 and electrophysiologic (EP) stimulation pulse signals. In particular, analog circuit 40 receives ECG signals from patient skin electrodes of ECG cable 60 (FIG. 1) and processes these signals before providing them to the remainder of the programmer system in a manner well known in the art. Isolated analog circuit 40 further operates to receive the EP stimulation pulses from an external EP stimulator for the purposes of non-invasive EP studies, as is also known in the art. Similarly, the PSA 70 includes an optical isolator. Typically, high voltage withstanding, optical isolators or opto-isolators of the types described in commonly assigned U.S. Pat. No. 5,448,997 (block 22) or as described in U.S. Pat. No. 4,742,831 provide this electrical isolation.

The permanent coupling of a PSA, e.g., PSA 70, with the programmer reduces its flexibility of use. There may be instances when the PSA is advantageously used simply as a temporary external pacemaker wherein the programmer 26 is superfluous to that function or presents an unnecessary risk. For example, stray voltages may be accidentally introduced into the programmer 26 and conducted to the PSA 70.

It is also desirable to enable communications between the system at the site where the patient is located and with more remote equipment within the same building or elsewhere at remote locations. There are references to inclusion of modems in various types of external instruments as set forth in U.S. Pat. Nos. 4,751,726, 5,425,373, 5,758,652, and 5,725,559, and in commonly assigned U.S. Pat. Nos. 4,593,284, 4,987,897, and 5,836,989. However, a programmer resident modem coupled to telephone lines presents serious electrical hazards to a patient coupled to the same programmer by ECG cables or PSA or DSA cables. Surge voltages can be transmitted over telephone lines that bear the risk of being conducted to the patient and causing fibrillation or other malignant tachyarrhythmia of the heart.

In addition, the operating speeds and characteristics of modems continue to evolve. Moreover the various ways of interconnecting with the Internet, various LANs and intranet systems and the characteristics of those systems continue to evolve. Furthermore, national and regional telecommunication systems and standards and regulations both vary and continue to change and evolve at differing rates. For all of these reasons, any given modem incorporated into a programmer can become obsolete or not possible to meet all conditions and standards encountered throughout the world.

Thus, the system including a programmer, IMD and PSA (or PDA) described above with reference to FIGS. 1 and 2 and including a built-in modem is deficient in a number of respects. It is desirable to increase the capabilities of the programmer and the IMD to increase the operating modes and parameters and increase the available therapy delivery options and monitoring capacity of the IMD. The types of permanent and temporary IMDs continue to evolve, and more than one IMD may be implanted in or carried by a given patient. In some cases, it may be desirable to obtain physiologic data and IMD data from more than one such IMD employing the same programmer or external instrument to gather, correlate and display, store print or transmit such data at the same time.

But, it is desirable to miniaturize and lighten the programmer and any other associated equipment as described. As the size of the programmer is reduced, it becomes more difficult to fit such additional components and features into it and to provide an adequate power supply for them.

Consequently, a need remains for further improvements in interface devices for programmers and other external equipment including communications lines that allow the size of the programmer to be minimized, that increase operating capabilities, and that minimize the risk that the patient will be endangered by hazardous voltages or currents transmitted through the connections made with the patient's body.

SUMMARY OF THE INVENTION

The present invention solves these problems identified with prior art external instruments including programmers, analyzers and other equipment and accessories used to test or communicate with IMDs involving interface devices that enable expansion of the capabilities while minimizing the space required and maintaining or increasing patient safety.

In one aspect of the invention, the invention is compatible with remote patient management systems that interact with remote data and expert data centers. Specifically, the invention provides a data communication link that is able to transfer clinical data from the patient to a remote location for evaluation, analysis, storage in data repositories, and clinical evaluation without exposing the patient to electrical hazards. The data communication link is compatible with various data mining and network communication systems such as the Internet, intranet and the World Wide Web.

The data communication link comprises in one embodiment, a modem card adapted to be inserted into and removed from a programmer at a modem connection terminal and an isolator in the programmer coupled to the modem connector to block hazardous electrical signals passing through the modem from reaching a patient coupled with the programmer. The appropriate modem drivers and associated software are readily loaded onto the programmer operating system disk drive. The removable and replaceable modem and modem software enables selection of the optimum modem for use in any country or region of the world.

In a further aspect of the invention, the programmer is formed having an expansion bay extending into its case that is adapted to receive a series of interchangeable expansion modules to extend the capabilities of the programmer. Each such module is formed having a housing that fits into the expansion bay in the housing of the programmer. Each such module is formed with module connector terminals adapted to mate with programmer connector terminals of an expansion bay interface connector when the module housing is seated in the expansion bay. The modules generally can expand memory capacity or provide signals to or receive signals from the on-board operating system and are rendered operational with software loaded onto the operating system hard drive when the module is used.

In this aspect of the invention, any such module that is coupled with the external environment that could conduct hazardous electrical signals into the programmer or from the programmer to the patient includes internal isolation of the module operating system to block such hazardous signals conducted on data lines and an isolated power supply to supply power to the module operating system. Such modules that present patient hazards may be a PSA and/or DSA module or a temporary pacing module or a cardioversion/defibrillation module that is coupled to the patient through pacing and/or cardioversion/defibrillation leads, respectively, that are in direct contact with the patient's heart. Or, the module may be a physiologic sensor module for sensing a physiologic parameter, e.g., blood pressure, temperature, pH, and gas concentrations, through an indwelling catheter or lead extending a sensor into the patient's body.

In accordance with this aspect of the present invention, the modules are preferably formed having an internal isolation barrier that isolates the module connector terminals that mate with the programmer connector terminals from the module operating system. Moreover, the expansion module preferably includes a battery back-up power source that can power the module operating system in case the programmer power supply fails or even if the module is removed from the expansion bay. In the latter case, the internal isolation barrier prevents any hazardous electrical signals from being conducted from the module connector terminals to the module operating system and from there to the patient's body.

In a variation of this aspect of the invention, the expansion bay interface connector terminals can also or alternatively be isolated within the programmer by an additional or alternate expansion bay signal interface comprising an opto-isolator and an isolated power supply.

In accordance with a still further aspect of the invention, testing of the IMD can be conducted while data is received from the IMD, and further data can be gathered from another IMD or auxiliary external medical devices employing a further analog signal input/output cable and box. For example, an IMD may be coupled to an expansion module for testing and recovery of data while the analog signal input/output cable and box are coupled with a physiologic sensor for sensing a physiologic parameter, e.g., blood pressure, temperature, pH, and gas concentrations, through an indwelling catheter or lead extending a sensor into the patient's body.

In yet another aspect of the invention, analog signal carrying cables, e.g., ECG cables to ECG electrodes on the patient's skin and analog signal cables extending to remote equipment, are adapted to be attached to cable connector terminals of the programmer. Such cables can conduct hazardous electrical signals into the programmer or from the programmer to the patient. The programmer includes optical isolators coupled with the cable connector terminals to block such hazardous signals.

Thus, the capabilities and flexibility of the instrument are magnified without unduly increasing size and weight, and safety systems are provided for protecting the patient from harm due to electrical potentials.

This summary of the invention the advantages and features thereof have been presented here simply to point out some of the ways that the invention overcomes difficulties presented in the prior art and to distinguish the invention from the prior art and is not intended to operate in any manner as a limitation on the interpretation of claims that are presented initially in the patent application and that are ultimately granted.

BRIEF DESCRIPTION OF THE DRAWINGS

These and other advantages and features of the present invention will be appreciated to those of skill in the art as the same becomes better understood by reference to the following detailed description of the preferred embodiment of the invention when considered in connection with the accompanying drawings, in which like numbered reference numbers designate like parts throughout the figures thereof, and wherein.

DETAILED DESCRIPTION OF THE PREFERRED EMBODIMENTS

Figure 3:
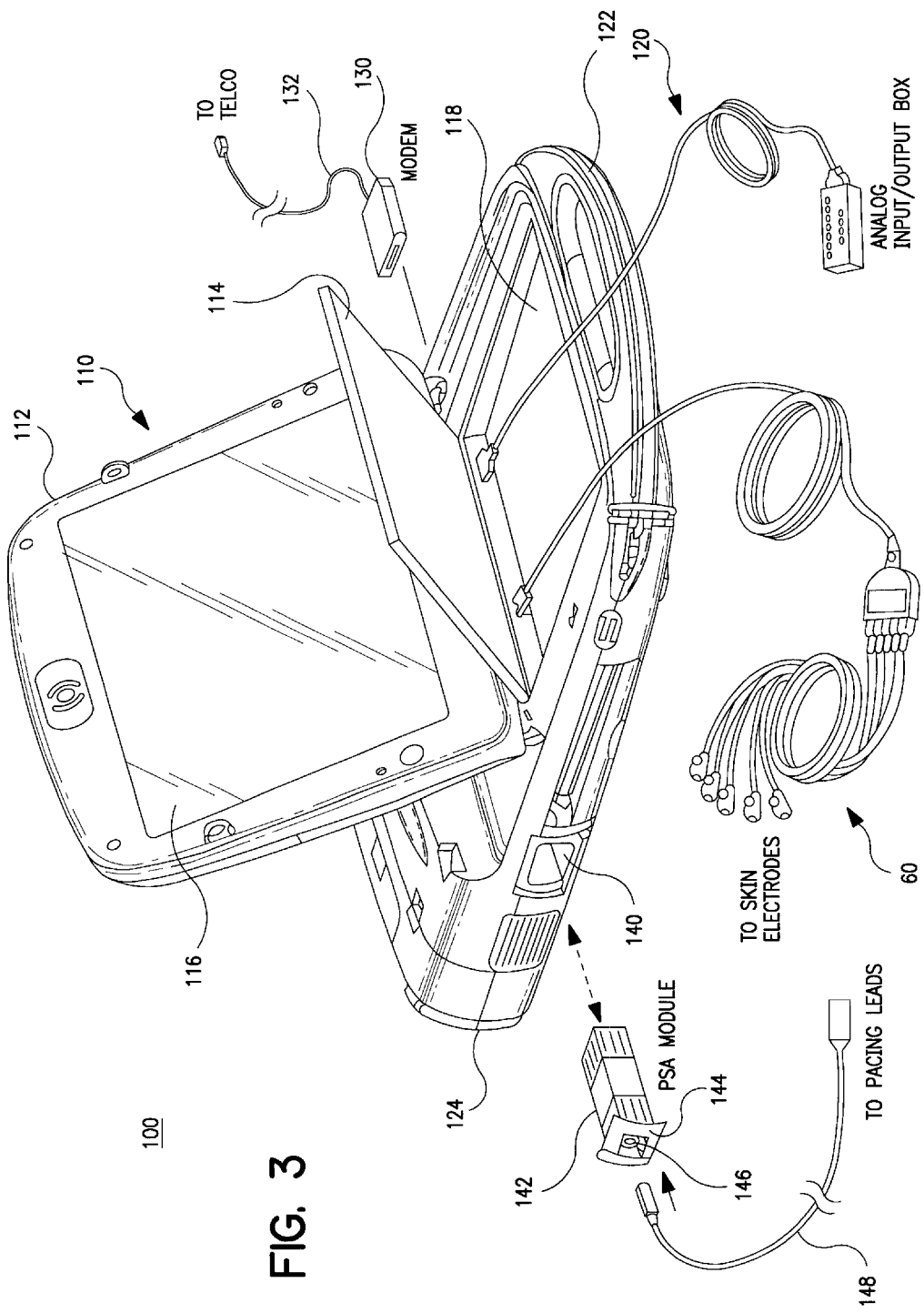
FIG. 3 is a simplified view of the improved instrument for programming, testing or communicating with an IMD and with remote equipment in accordance with various aspects of the present invention.

FIG. 3 illustrates an improved instrument 100 comprising programmer 110 and a number of accessories that provide a number of capabilities for testing, monitoring, and programming an IMD including an IPG and associated leads, for example, and for communicating data and operating commands to and from remote equipment. The external configuration of the programmer 110 is also depicted in commonly assigned U.S. Design Pat. No. D438,204S.

Figure 1:
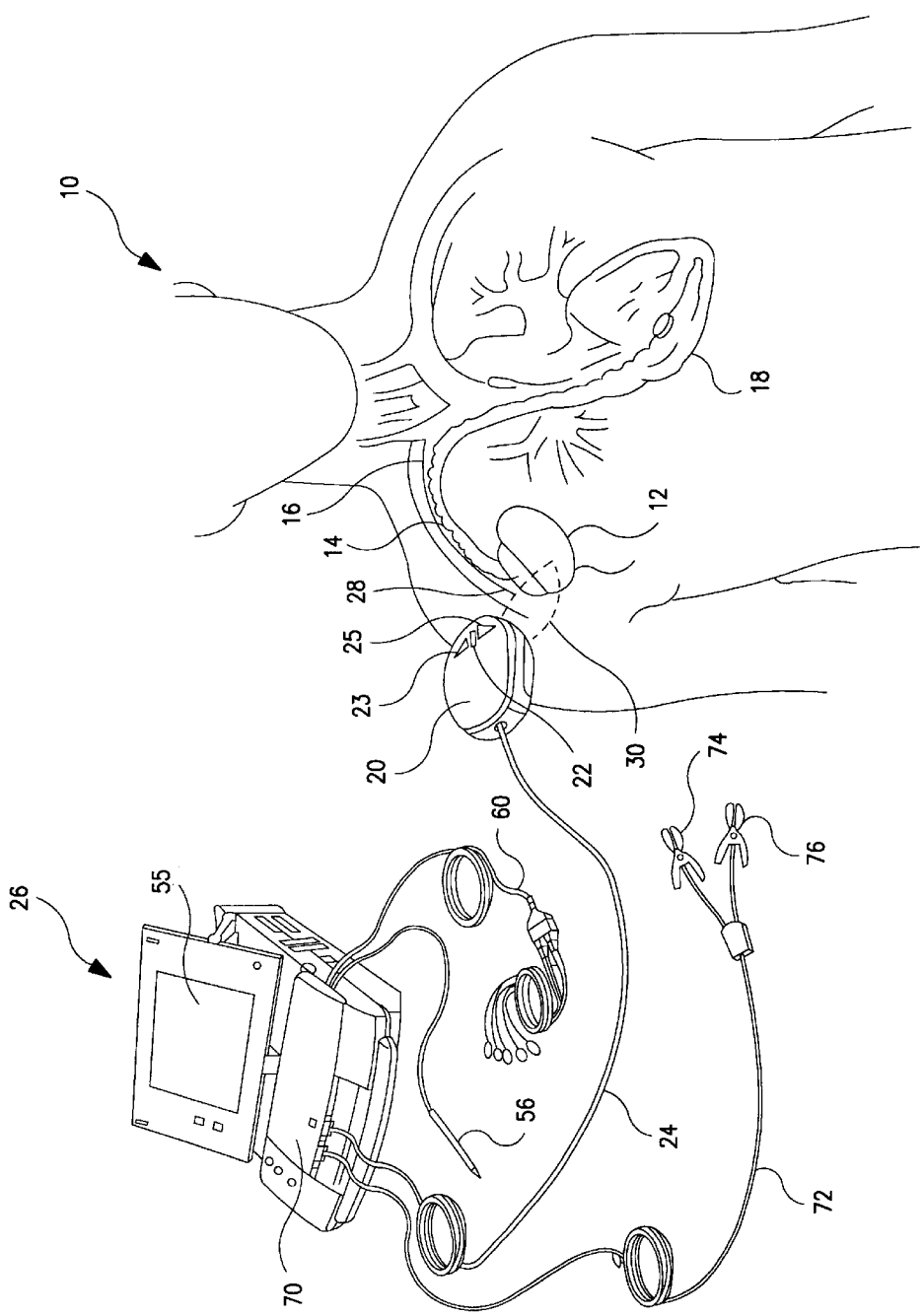
FIG. 1 is a simplified view of an IMD and a prior art external programmer and analyzer.
Figure 2:
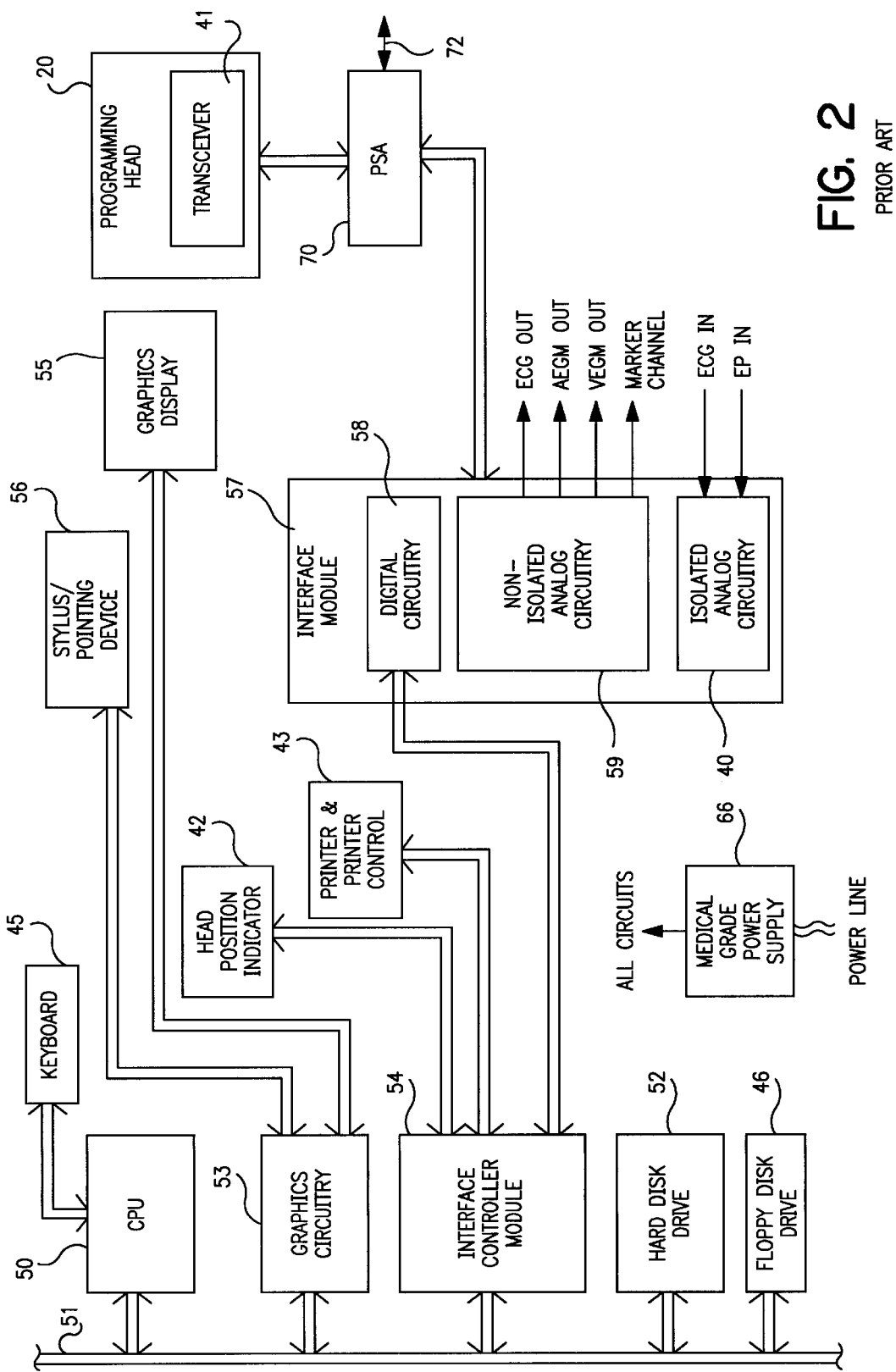
FIG. 2 is a simplified circuit block diagram of major functional blocks of the prior art external programmer of FIG. 1.

The programmer 110 includes an outer cover 112 and an inner cover 114 that are both shown in their open positions above the case. The inner cover 114 is hinged to lift to the depicted open position and to reveal a compartment 118 for storing the ECG cable 60, an analog input/output cable and box 120, a stylus (not shown), and a programming head (not shown). The inner cover 114 has a soft key keyboard on its upper surface that is obscured in the open position but overlies the compartment 118 in the closed position. The outer cover 112 is hinged to be opened to the depicted open position to reveal the display 116 and to be closed orienting the display 116 facedown over the keyboard and providing a slim profile for the programmer 110. A handle 122 is provided to facilitate moving the programmer 110 about. While a conventional programming head 20 of FIG. 1 can be employed, one or more antenna can be formed in the case or outer cover 112 for high frequency telemetry with IMDs at a distance. A number of other input/output terminals, bays and connectors are arranged about the periphery 124 of the case to receive a floppy disk or CD or the like to load software onto the hard disk drive or other programmer memory. A power connection is made by a power cord attached at a power terminal (not shown).

Figure 4:
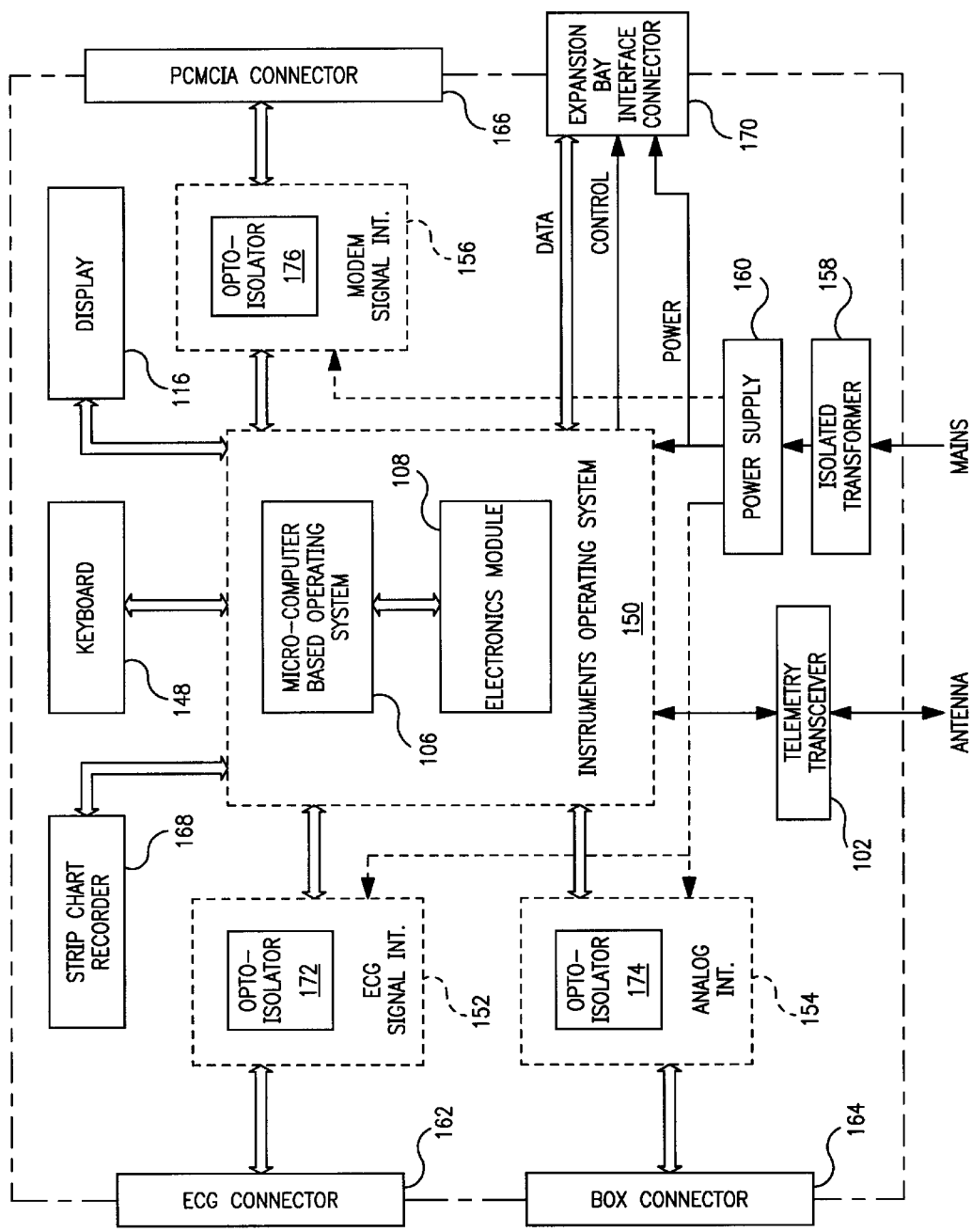
FIG. 4 is a simplified bock diagram of the major functional blocks of the instrument of FIG. 3 illustrating the electrical isolation of the patient from a variety of potential electrical hazards.
Figure 6:
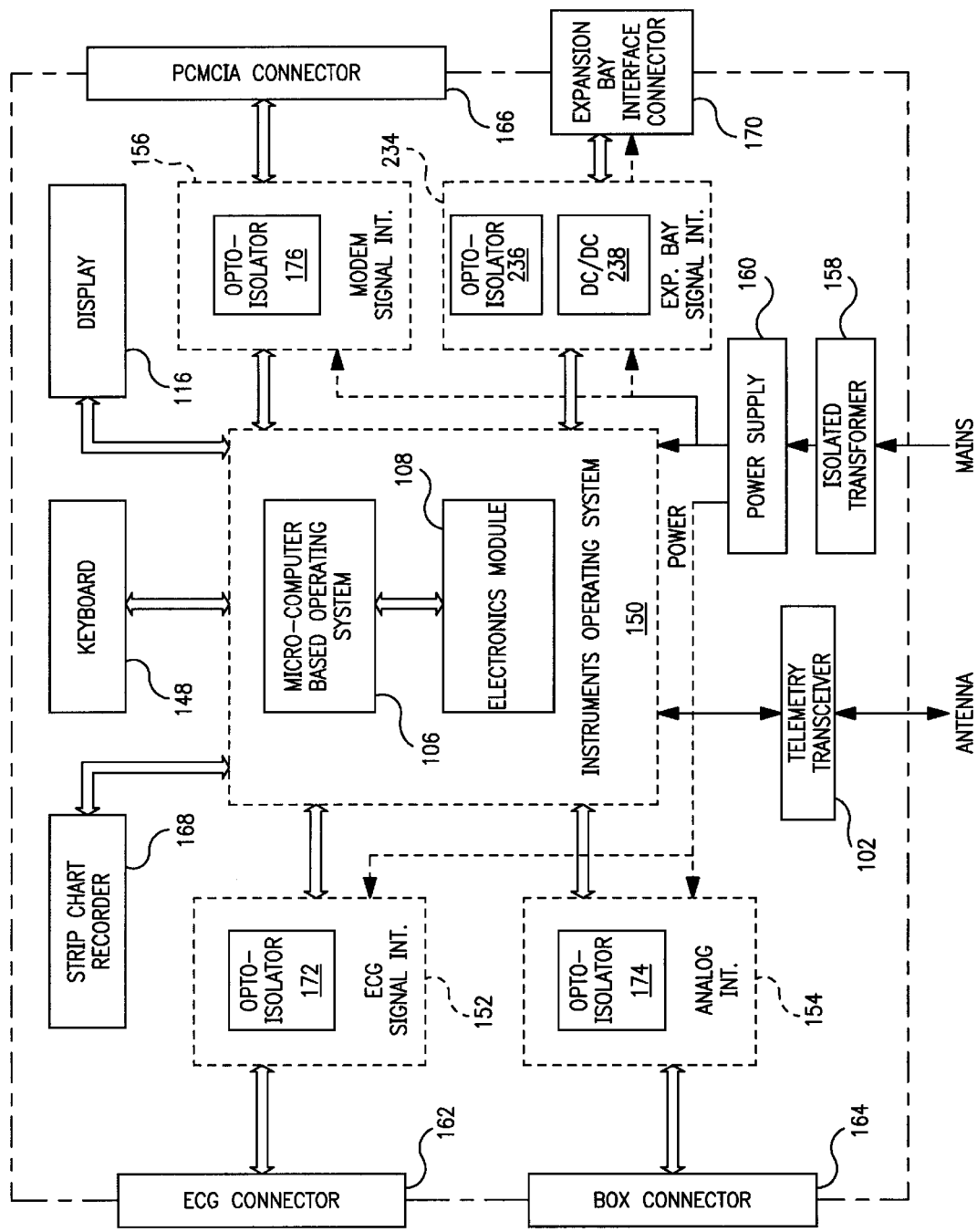
FIG. 6 is a variation of the simplified bock diagram of the major functional blocks of the instrument of FIG. 3 illustrating the electrical isolation of the patient from a variety of potential electrical hazards.

The electrical circuitry of the programmer 110 includes a number of the blocks depicted in FIGS. 4 and 6, including a PC-based hardware and firmware system 106 and an associated electronics module 108. Various functions and roles can be assigned to the PC-based hardware and firmware system 106 and the associated electronics module 108. The PC-based hardware and firmware system 106 preferably employs a CPU, RAM and ROM memory, an internal disk drive, video and audio cards, floppy disk drives, CD bays, and other components and peripheral devices typically associated with an IBM compatible personal computer that can be readily reprogrammed and updated. Typically, operating system software resident on the disk drive operates the PC-based hardware and firmware system 106, controls programmer functions including the keyboard 148 and display 116, and PCI communications with the a micro-computer based signal processing system 108. The signal processing system 108 preferably includes firmware and serial I/O ports for controlling and communicating with the telemetry transceiver, for processing ECG signals, routing analog data to and from the analog cable and box 120, transmitting data to and receiving data from the modem 130, and transmitting and receiving data and control signals with PSA module 142 (or any other expansion module in the expansion bay 140). However these functions and roles can be modified and shared between the PC-based hardware and firmware system 106 and the electronics module 108 in a variety of ways.

In accordance with one aspect of the present invention, an expansion bay 140 is formed extending from the periphery 124 into the case that is adapted to receive a series of interchangeable modules to extend the capabilities of the programmer 110. The expansion module generally can expand memory capacity or provide signals to or receive signals from the on-board operating system and are rendered operational with software loaded onto the system hard drive when the module is used. The expansion module can be a PSA and/or DSA module or a temporary pacing module or a cardioversion/defibrillation module that is coupled to the patient through pacing and/or cardioversion/defibrillation leads, respectively, that are in direct contact with the patient's heart. Or, the expansion module can be a physiologic sensor module for sensing a physiologic parameter, e.g., blood pressure, temperature, pH, and gas concentrations, through an indwelling catheter or lead extending a sensor into the patient's body.

For example, a PSA module 142 is shown in FIG. 3 that is adapted to be coupled through PSA cable 148 to the pacing leads to conduct lead testing and pacing and sensing threshold measurements upon implantation of the lead as described above with reference to FIG. 1. The PSA cable 148 may take the form of the cable disclosed in commonly assigned U.S. Pat. No. 5,782,892 or 5,931,861, for example. The proximal end of the PSA cable 148 is adapted to be inserted into a terminal 146 of the PSA module 142. A series of LED display lights 144 are arranged on the face of the PSA module 142 that are lighted to indicate paced and sensed events. In addition, the analyzer software provides on-screen displays of the pacing, sensing, and measurement functions of the PSA module 142 on display 116. The clinician can change stimulation parameters by selecting them from a menu displayed on display 116.

In accordance with another aspect of the invention, a PCMCIA card receiving slot and connector (obscured in FIG. 3) are provided in periphery 124 to receive a PCMCIA modem 130 that is adapted to be connected to a telephone line by the telephone cable 132 (or other communication link) to enable communications to and from the programmer 110 and remotely located equipment. These communications may be through an installed LAN and intranet connection or through the Internet by way of optical fiber or wire lines, satellite transmission or any available means. The coupling of the modem 130 through a hard-wired telephone cable 132 raises the risk that line voltages induced on the system from external sources could be conducted to the patient through the internal circuitry of the instrument 100 and through the PSA module 142 and PSA cable 148 coupled with the pacing leads or through the ECG cable and to the skin electrodes.

In accordance with a still further aspect of the invention, testing of the IMD can be conducted while data is received from the IMD, and further data can be gathered from another IMD or auxiliary external medical devices employing the analog signal input/output cable and box 120. For example, an IMD may be coupled to an expansion module for testing and recovery of data while the analog signal input/output cable and box 120 are coupled with a physiologic sensor for sensing a physiologic parameter, e.g., blood pressure, temperature, pH, and gas concentrations, through an indwelling catheter or lead extending a sensor into the patient's body. Alternatively, analog data that is developed in use of the expansion module and/or the ECG cable and electrodes can be routed to a further remotely located instrument coupled to the analog signal input/output cable and box 120.

But, hazardous electrical signals transmitted through the analog input/output cable and box 120 can also be conducted to the patient through the internal circuitry of the instrument 100 and through the expansion module, e.g., the PSA module 142 and PSA cable 148 coupled with the pacing leads, or through the ECG cable and to the skin electrodes.

Moreover, voltages induced within the operating system from any source can be conducted to the patient through the internal circuitry of the instrument 100 and through the PSA module 142 and PSA cable 148 coupled with the pacing leads or through the ECG cable and to the skin electrodes.

FIGS. 4 and 6 illustrate the electrical isolation of the patient from a variety of potential electrical hazards in at least two possible configurations. The power supply 160 susceptible to picking up hazardous high voltages is isolated within the programmer by transformer 158 that provides 4,000 volts protection. Data bus and/or control and/or signal routing lines connect the operating system to the keyboard 148, the display 116, a strip chart printer or recorder 168, the expansion bay interface connector 170, and the ECG connector 162, the box connector 164, and the PCMCIA connector 166 through signal interfaces 152,154,156, respectively. The signal interfaces 152,154,156 include opto-isolators 172,174, and 176, respectively, that optically transmit electrical signals, typically encoded data, to and from an expansion module inserted into the bay 140, including the PSA module 142, to and from the PCMCIA modem 130, from the ECG cable 60, and to and from the analog input/output cable and box 120. In each case, the signal interface circuitry and the opto-isolators can take the form shown and described in commonly assigned U.S. Pat. No. 5,448,997 or a modification thereof that enables transmission of analog and digital signals through the signal interface circuitry as necessary in each case. Each opto-isolator 172, 174 and 176 preferably comprise one or a plurality of individual opto-isolator elements that each provide 1500 volts isolation.

In certain cases, DC power from the instrument power supply is also coupled to a module inserted into the bay 140, including the PSA module 142, to the PCMCIA modem 130, to the ECG cable 60, and over dedicated power conductors of the analog input/output cable and box 120. Therefore, the signal interfaces 152, 154 and 156 can include DC/DC converters for providing isolated DC power to DC power terminals of the ECG connectors 62, the box connector 164, and the PCMCIA connector 166.

ECG Cable Isolation

The ECG cable connector 162 is coupled to ECG signal interface circuitry 152, and high voltages induced upon or picked up by the ECG cables connected with ECG cable connector 162 are not passed by the opto-isolator 172 to the instrument operating system 150.

Analog Cable and Box Isolation

The analog input/output box connector 164 is coupled to analog signal interface circuitry 154 including an analog signal opto-isolator 174. High voltages transmitted through the analog input/output cable and box 120 connected with input/output box connector 154 are blocked by the opto-isolator 174 from passing to the instrument operating system 150.

PCMCIA Isolation

Similarly, the PCMCIA input/output connector 166 is coupled to the modem signal interface circuitry 156 including the modem signal opto-isolator 176, and high voltages that may be transmitted through the modem 130 are blocked from passing to the instrument operating system 150 by the opto-isolator 176.

Expansion Module Isolation

In most cases, the module inserted into the expansion bay 140 is powered by DC power from the programmer power supply 160 and digital command, control and data signals are exchanged between the module and programmer through power supply and digital signal terminals, respectively, of the expansion bay interface connector 170. The expansion bay 140 and expansion bay interface connector 170 are designed to accommodate the above-described PSA module 142 and other modules that may not or may not be connected to the patient or to equipment susceptible to picking up high voltages. For example, the expansion bay 140 and expansion bay interface connector 170 are designed to receive various types of memory devices to increase memory capacity that would not be connected to the patient or to equipment susceptible to picking up high voltages. On the other hand, the expansion bay 140 and expansion bay interface connector 170 are designed to receive other test and stimulation modules, e.g., the above-described PSA or a temporary pacemaker for temporarily pacing the patient's heart through temporarily implanted leads or to a monitor that monitors physiologic conditions of the heart or vascular system through indwelling catheter or lead borne sensors, e.g., blood pressure sensors. In each of these cases, the patient is susceptible to being shocked into fibrillation by high voltages conducted to the heart through a conductor of the indwelling catheter or lead.

Figure 5:
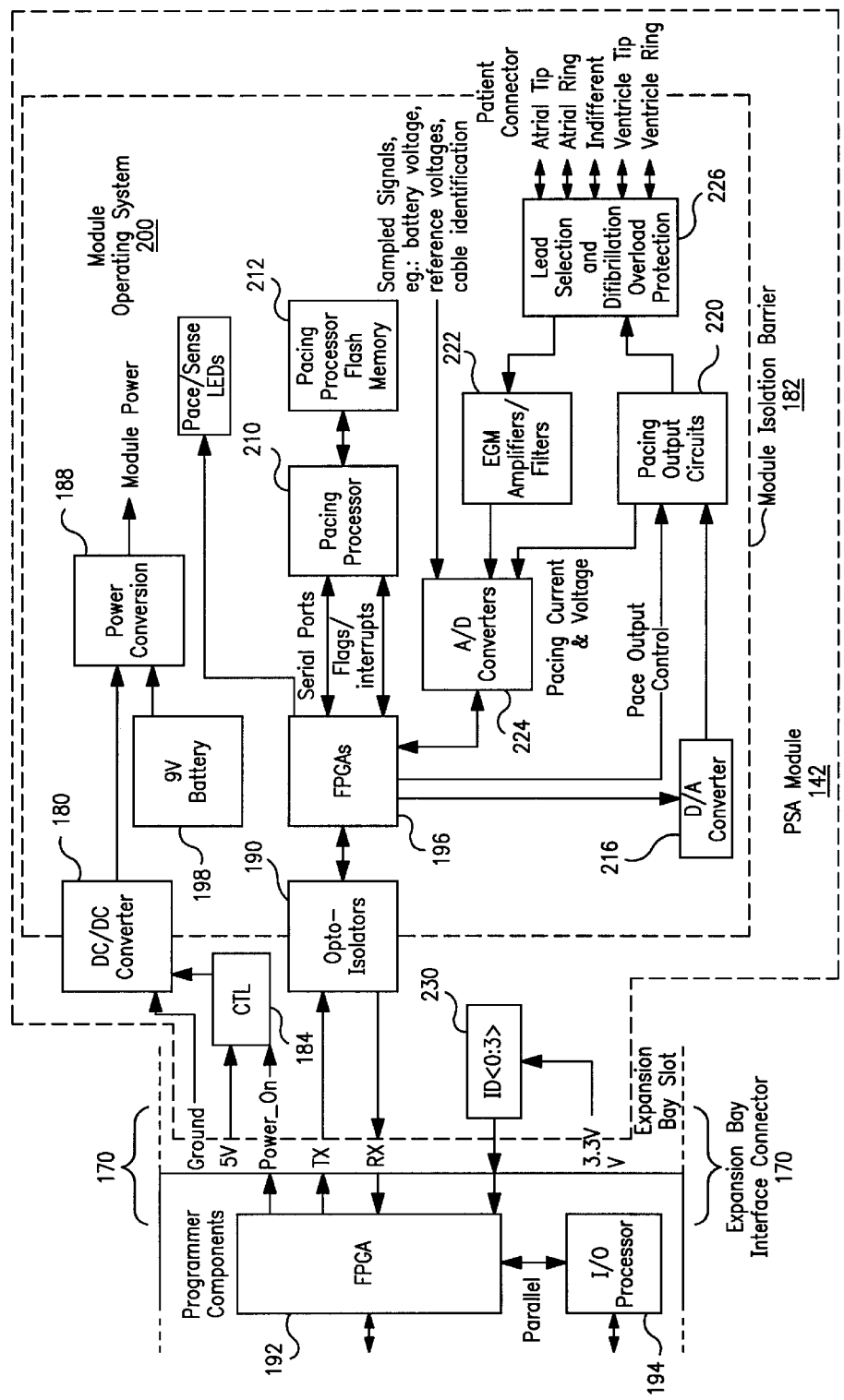
FIG. 5 is a simplified block diagram of the circuitry of a PSA module adapted to be inserted into an expansion bay interface connector, the module circuitry incorporating electrical power supply and command and data signal isolation for patient safety.

Consequently, in these cases, the circuitry of the PSA module 142 adapted to be inserted an expansion bay interface connector 170, the circuitry incorporating electrical isolation for patient safety as shown in FIG. 5. DC power is delivered to the module operating system within PSA module 142 through a power isolator resident in the module circuitry of FIG. 5, and the digital data and command signals exchanged between the programmer 110 and the PSA module 142 pass through an opto-isolator resident in the module circuitry of FIG. 5.

The PSA module 142 design is based on the MEDTRONIC® Model 8090 PSA. All of the features of the Medtronic® Model 8090 PSA are included in the PSA module 142. The PSA module 142 differs from the Model 8090 PSA in that the communication interface has been modified to allow it to function with the programmer 110 as described herein.

In accordance with this aspect of the present invention, the PSA module 142 and other expansion modules adapted to be coupled to the patient are formed having an internal module isolation barrier 182 that isolates the module connector terminals that mate with the programmer connector terminals from the module operating system 150. Moreover, the PSA module 142 preferably includes a battery back-up power source that can power the module operating system 200 in case the programmer power supply fails or even if the module is removed from the expansion bay 140. In the latter case, the internal isolation barrier 182 prevents any hazardous electrical signals from being conducted from the module connector terminals to the module operating system and from there to the patient's body.

The PSA module operating system 200 shown in FIG. 5 is a microprocessor-based system intended to assess the pacing and sensing performance of atrial and ventricular cardiac pacing leads of a pacemaker or ICD during implantation as described above. The application software for the PSA module 142 is installed onto the hard disk drive of the programmer 110. Software installed in memory of the programmer 110 provides on-screen displays of the pacing, sensing, and measurement functions of the PSA module 142. The software provides the clinician with the ability to change the configuration or operating parameters of the PSA module 142. Changes include lead polarity, pacing modes, pacing amplitudes, pulse widths, and measurement queuing. The firmware controls timing of the delivered pacing pulses based on the pacing mode selected and the patient's intrinsic events. The blanking intervals, refractory periods, mode operations, and transitions between pacing modes are performed by the firmware. The firmware provides the PSA module 142 access to the following pacing modes: AOO, VOO, DOO, ODO, AAI, VVI, VDD, and, DDD.

The following test and display operations of the PSA module 142 are identical to that of the MEDTRONIC® Model 8090 PSA but are performed in a different manner under the control of the programmer 110, the application software and the firmware. Typical lead assessments performed by the PSA module 142 include:

Sensing Measurements (Amplitude and Slew Rate Measurements of P & R Waves)
  Amplitude and slew rate measurements are taken to test for optimal lead position. Optimal lead positioning ensures minimal problems with under and over sensing.
Stimulation Threshold Measurements
  Voltage stimulation thresholds are used to determine appropriate pacing margins.
Lead Impedance Measurements
  Impedance measurements provide an indication of lead integrity. The presence of fractures in the lead insulation or wiring as well as electrical shorts within the conducting portion of the lead can be detected by impedance measurements
Antegrade & Retrograde Conduction Tests
  The PSA 142 provides tests for determining the patient's conduction characteristics. The antegrade assessment initiates atrial pacing and a beat-to-beat display of the patient's atrial to ventricular conduction interval. The retrograde assessment initiates ventricular pacing and a beat-to-beat display of the patient's ventricular to atrial conduction interval.
Retrograde Measurements
  Retrograde measurements are used to determine if paced ventricular activity conducts back to the atrium. Results of this measurement are useful in selecting the appropriate atrial refractory period for the pacemaker.
Automatic Measurement of P & R Wave Amplitudes and Slew Rates
  When pacing is inhibited, the PSA 142 provides beat-to-beat measurement of the patient's intrinsic P and/or R wave amplitudes and slew rates.
Automatic Lead Impedance Measurement
  When pacing is initiated from the PSA 142, the PSA 142 automatically determines the pacing impedance on the first pacing pulse. Subsequent measurements are available via an impedance button.
Real Time Display of Atrial and Ventricular EGM
  The PSA module 142 operating in conjunction with the ECG cable 60 and programmer 110 provides real time displays of surface ECG traces, and intracardiac atrial and ventricular EGMs. Pace and sense markers are also provided to assist with interpretation of device operation. The real time waveforms provide the operator with a means to rapidly determine pacing thresholds and assess the patient's intrinsic conduction characteristics. An advanced feature for high-resolution display of single atrial or ventricular complexes is also available. This single complex display allows the physician to view the morphology of the intracardiac waveforms.
Rapid Atrial Stimulation to 800 PPM
  The PSA 142 can deliver rapid atrial stimulation at rates up to 800 PPM for treating atrial arrhythmias. An option to deliver ventricular pacing at the selected lower rate during rapid atrial stimulation has also been included.
Pulse Width Versus Amplitude Threshold Assessment
  The PSA 142 has the ability to determine pacing thresholds at a number of output amplitudes and pulse widths. Each threshold is plotted on a graph to allow the physician to generate a strength duration curve of the pacing characteristics of a given lead position.

Measurement Reports

The PSA 142 provides a means to generate hard copy reports for lead measurements, frozen waveforms and pulse width/amplitude graphs. All reports are generated on strip chart recorder 168 contained within the programmer 110.

Each expansion module is identifiable by an ID tag 230 providing ID bits to the programmer 110, so that the programmer 110 recognizes the expansion module when it is inserted into the expansion bay. The programmer operating system 150 automatically launches a program to support the expansion module when it is identified.

The DC/DC converter 180 and opto-isolators in opto-isolators block 190 provide the module isolation barrier 182 to ensure high voltage isolation of the PSA module 142 from the programmer operating system 150 or from any stray electrical signal or discharge that contacts the module connector terminals when the PSA module 142 is not inserted into the expansion bay 140. The PSA module power conversion circuit 188 receives power from the DC/DC converter 180 or the battery 198 and supplies it to the various powered circuits and components of the module operating system 200 of PSA module 142.

When inserted into the expansion bay 140, the PSA module 142 receives 5 volt DC power and a ground connection from the programmer power supply 160 through a control circuit 184 coupled with power terminals of the expansion bay interface connector 170. The ground connection is made first so that the insertion and removal can take place without powering down the programmer operating system 150. The control circuit 184 is turned on by a Power_On signal provided by the instrument operating system 150 when the clinician commences a PSA operation by inserting the PSA module 142 into the bay 140 and selecting it's operation from a displayed menu. The DC/DC converter 180 provides 1500 volts protection in order to isolate the PSA patient cable 148 from the other programmer input/output circuits and the power supply 160.

The PSA module 142 also accepts the 9-volt battery 198 that is used to provide back-up power in the event of loss of programmer power during pacing or when the PSA module is removed from the expansion bay 140. This battery is intended to provide short-term support while system power is restored, or while interim pacing support is connected. The clinician will be able to observe the operation of the PSA module 142 when the programmer display and input are not available by viewing the pace and sense LED indicators on the PSA module 142 case while operating from the back-up battery. The PSA module 142 switches back to the programmer power source 160 when programmer power is re-established while the PSA module 142 is operating from the backup battery.

The transfer of PSA module control data, including digitized control signals, pacing parameter programming commands (e.g., pacing pulse widths, pulse amplitudes, AV delay, pacing rate, etc., attendant to DDD pacing) and digitized module test data, e.g., lead impedance data, between the programmer 110 and the PSA module 142 is effected through the expansion bay interface connector 170. The PSA control data from the programmer operating system 150 passes through a PSA data path TX, and the test data passes through a PSA data path RX. The isolated PSA data paths TX and RX traverse the opto-isolators circuit 190 that is coupled between field programmable gate array (FPGA) 192 of the programmer operating system 150 and first and second FPGAs 196 of the PSA operating system 200 through data terminals of the expansion bay interface connector 170. FPGAs are programmable components that can be configured to perform a wide variety of operations. Their primary benefit is that they incorporate the functions typically performed by a large number of components into a single chip, thereby reducing component count and increasing reliability. The opto-isolators circuit 190 transfers PSA data between the FPGAs 192 and 196 optically, rather than electrically, thereby providing/preserving the isolation of the patient from harmful voltages and leakage currents from the programmer 110.

The pacing circuitry contains a digital signal processor (DSP) in pacing processor circuitry 210 that is responsible for performing all of the pacing, sensing and measurement functions. The pacing processor 210 operates in accordance with PSA data programming commands received from the programmer 110 through the isolated DSP data path TX. The pacing processor 210 returns measurements, pace/sense markers, and real-time atrial/ventricular EGMs as DSP data through DSP data path RX. The firmware that the pacing processor 210 executes to perform its pacing, sensing and measurement functions is contained in the pacing processor flash memory 212. Flash memory 212 is originally programmed during installation of the PSA module 142 into the expansion bay 140. The flash memory 212 can be re-programmed in the field using the programmer 110 should new features or measurement techniques be developed.

The pacing processor 210 controls the atrial and ventricle pacing output circuits within pacing output circuitry 220. The atrial and ventricle pacing output circuits are separate circuits with the exception of the virtual ground amplifier and current measurement circuits that are shared.

The pacing processor 210 sets the pacing pulse amplitude by programming the digital-to-analog (D/A) converter 216 to a specified amplitude digital signal received via DSP data path TX. The amplified output of the D/A converter 216 charges a holding capacitor of the pacing output circuits to the specified amplitude. The pacing pulse width is controlled by DSP pacing processor 210 software using processor output flags. The length of time the firmware asserts a pacing output flag, determines the width of the pacing pulse. When the pacing flag is de-asserted the hardware will automatically perform the pacing recharge cycle. The pacing rate is determined by the frequency that the software asserts the pacing output flags.

The pacing output circuits 220 are coupled to selected connectors in lead selection and defibrillation overload protection circuitry 226 selection for connection with the selected pacing leads. The selected connectors also connect the selected leads to EGM and sense event circuits within the EGM amplifiers/filters circuitry 222 to process selected atrial and/or ventricular EGM signals. EGM sampling, sense amplifier filtering, atrial and ventricular (P/R) sense event detection, atrial and ventricular (P/R) EGM amplitude measurements, and slew rate measurements are performed by software using DSP algorithms applied to the sampled EGM data.

The slew rate is the rate of change of the unfiltered intrinsic depolarization, and is measured in volts per second. Slew rate is calculated by determining the maximum rate of change of the depolarized waveform.

The sense amplifier algorithm consists of a digital band pass filter to remove signals outside of the expected frequency range of cardiac signals. The software then takes the absolute value of the filtered EGM signal and compares it to a sense threshold. If the signal exceeds the sense threshold, a sense event has occurred causing the pacing processor 210 to take the appropriate action based upon the pacing mode of the PSA module 142. The sense threshold is programmable by selecting a sensitivity setting within the PSA module 142.

The P/R amplitude measurements are base-to-peak amplitude measurements of P/R wave signals that have caused sense detects. The P/R wave amplitude measurements are taken after the EGM signal has been passed through the digital band pass filter and an absolute value algorithm Sensing is performed by comparing the output of the DSP filter algorithm against a programmed threshold level. If that level is surpassed then a sensed event is declared. Sensed events are reported to the programmer via markers that are placed in the EGM data stream. Timing is atrial based in dual chamber sensing modes.

The firmware enables a variety of measurements for use in lead analyses. Each pacing pulse can be measured for lead impedance and pacing current delivered. Each sensed event can be measured for amplitude and slew rate. The firmware also monitors the condition of the backup battery and the identity of the cable attached to the cable/adaptor port.

Although the preferred embodiments of the present invention have been described in the context of a Medtronic programming system, it will be appreciated that the following claims are not so limited or confined but are instead applicable to programming or telemetry systems of any manufacturer for any IMD or implant. Those of skill in the art will be readily able to apply the teaching found herein to yet other embodiments within the scope of the following claims.

Returning to FIG. 6, it depicts a variation on the instrument operating system including a further expansion bay signal interface 234 inserted between the expansion bay interface connector 170, the power supply 160, and the instrument operating system 150. The expansion bay signal interface 234 includes an opto-isolator 236 that operates the same as the opto-isolator 190 and a DC/DC converter 238 that operates in the same manner as the DC/DC converter 180. The expansion bay signal interface 234 can be in addition to or a substitute for the DC/DC converter 180, the control 184 and the opto-isolator 190. Each of the other interfaces 152, 154 and 156 may include a DC/DC converter that can isolate power lines of the equipment coupled with the connectors 162, 164 and 166.

Although the preferred embodiments are described in relation to a programmer, it will be understood that the principles of the invention may be applied to other instruments that may not have all of the capabilities of such a programmer of an IMD or multiple IMDs in a single patient or that may have additional and alternate capabilities.

The United States patents and any other documents referenced herein are all incorporated by reference herein.

Although particular embodiments of the invention have been described herein in some detail, this has been done for the purpose of providing a written description of the invention in an enabling manner and to form a basis for establishing equivalents to structure and method steps not specifically described or listed. It is contemplated by the inventors that the scope of the limitations of the following claims encompasses the described embodiments and equivalents thereto now known and coming into existence during the term of the patent. Thus, it is expected that various changes, alterations, or modifications may be made to the invention as described herein without departing from the spirit and scope of the invention as defined by the appended claims.

What is claimed is:

1. In an external medical instrument to communicate with implantable medical devices (IMDs) implanted in the patient's body and capable of communicating with other medical instruments located at a distance from the patient, a safety system for protecting the patient from harm due to hazardous electrical signals comprising:

an expansion bay of the external medical instrument adapted to receive a module expanding the capabilities of the external medical instrument, the expansion bay further comprising an expansion bay interface connector;

a module fitted into the expansion bay and connected with the expansion bay interface connector having a module operating system;

a cable coupling the module operating system with the patient's body for conducting electrical signals to and from the patient's body;

an instrument operating system that creates and transmits module control data through the expansion bay interface connector in a transmission data path to the module operating system and receives module test data through the expansion bay interface connector in a reception data path from the module operating system; and an opto-isolator within the module and in the transmission data path and the reception data path for isolating the instrument operating system from the module operating system to block passage of hazardous electrical signals through the cable to the patient's body.

2. The safety system of claim 1, further comprising:

an electrical power supply within the instrument coupled with an external power line that provides electrical power to the instrument operating system through an electrically isolated power transformer for blocking passage of hazardous electrical signals conducted through the external power line to the instrument operating system; and means for providing electrical power to the module operating system through the expansion bay interface connector including an electrically isolated power transformer that isolates the module operating system from hazardous electrical signals.

3. The safety system of claim 1, further comprising:

an analog signal cable interface connector coupled with the instrument operating system adapted to pass analog data to a remote instrument through an analog data transmission cable;

an elongated analog data transmission cable having a first end coupled with the analog signal cable interface connector and a second end coupled with a remote instrument; and analog signal interface circuitry including an opto-isolator for conducting analog signals between the analog signal cable interface connector and the instrument operating system and for blocking hazardous electrical signals passing through the analog data transmission cable from the remote instrument.

4. The safety system of claim 1, further comprising:

an ECG cable interface connector coupled with the instrument operating system adapted to be coupled with an ECG cable to pass ECG data to the instrument operating system;

an elongated ECG cable having a first end coupled with the ECG cable interface connector and a second end coupled with a plurality of ECG electrodes adapted to be applied to the skin of a patient's body; and ECG signal interface circuitry including an opto-isolator for conducting ECG analog signals between the ECG cable interface connector and the instrument operating system and for blocking the conduction of hazardous electrical signals through the ECG cable interface connector.

5. In an external medical instrument in physical contact with a patient's body to communicate with or test the function of imptantable medical devices (IMDs) implanted in the patient's body or to measure a physiologic condition of the patient's body and capable of communicating with other medical instruments or systems located at a distance from the patient, a safety system) for protecting the patient from harm due to hazardous electrical signals comprising:

an expansion bay of the external medical instrument adapted to receive a module expanding the capabilities of the external medical instrument, the expansion bay further comprising an expansion bay interface connector;

a module fitted into the expansion bay and connected with the expansion bay interface connector having a module operating system;

a cable coupling the module operating system with the patient's body for conducting electrical signals to and from the patient's body;

an instrument operating system that creates and transmits module control data through the expansion bay interface connector in a transmission data path to the module operating system and receives module test data through the expansion bay interface connector in a reception data path from the module operating system; and an opto-isolator within the module and in the transmission data path and the reception data path for isolating the instrument operating system from the module operating system to block passage of hazardous electrical signals through the cable to the patient's body;

wherein the external medical instrument is an external programmer for receiving information-encoded, telemetry uplink signals transmitted from a IMD telemetry antenna and transmitter circuit in the IMD in a telemetry uplink transmission and for transmitting information-encoded telemetry downlink signals from a programmer telemetry antenna in a telemetry downlink transmission.

6. The safety system of claim 5, further comprising:

an electrical power supply within the instrument coupled with an external power line that provides electrical power to the instrument operating system through an electrically isolated power transformer for blocking passage of hazardous electrical signals conducted through the external power line to the instrument operating system; and means for providing electrical power to the module operating system through the expansion bay interface connector including an electrically isolated power transformer that isolates the module operating system from hazardous electrical signals.

7. The safety system of claim 5, further comprising:

an analog signal cable interface connector coupled with the instrument operating system adapted to pass analog data to a remote instrument through an analog data transmission cable;

an elongated analog data transmission cable having a first end coupled with the analog signal cable interface connector and a second end coupled with a remote instrument; and analog signal interface circuitry including an opto-isolator for conducting analog signals between the analog signal cable interface connector and the instrument operating system and for blocking hazardous electrical signals passing through the analog data transmission cable from the remote instrument.

8. The safety system of claim 5, further comprising:

an ECG cable interface connector coupled with the instrument operating system adapted to be coupled with an ECG cable to pass ECG data to the instrument operating system;

an elongated ECG cable having a first end coupled with the ECG cable interface connector and a second end coupled with a plurality of ECG electrodes adapted to be applied to the skin of a patient's body; and ECG signal interface circuitry including an opto-isolator for conducting ECG analog signals between the ECG cable interface connector and the instrument operating system and for blocking the conduction of hazardous electrical signals through the ECG cable interface connector.

9. In an external medical instrument to communicate with implantable medical devices (IMDs) implanted in the patient's body and capable of communicating with other medical instruments located at a distance from the patient, a safety system for protecting the patient from harm due to hazardous electrical signals comprising:

an expansion bay of the external medical instrument adapted to receive a module expanding the capabilities of the external medical instrument, the expansion bay further comprising an expansion bay interface connector;

a module fitted into the expansion bay and connected with the expansion bay interface connector having a module operating system;

a cable coupling the module operating system with the patient's body for conducting electrical signals to and from the patient's body;

a modem interface connector of the external medical instrument adapted to receive a modem;

a modem connected with the modem interface connector and with a data transmission network through a modem data cable, the modem adapted to transmit patient and IMD data to and from a remote location of a network;

an instrument operating system that creates and transmits module control data through the expansion bay interface connector in a transmission data path to the module operating system and receives module test data through the expansion bay interface connector in a reception data path from the module operating system and that creates and transmits patient and IMD data through the modem to the remote location;

an opto-isolator within the module and in the transmission data path and the reception data path for isolating the instrument operating system from the module operating system to block passage of hazardous electrical signals through the cable to the patient's body including hazardous signals conducted through the modem interface connector to the instrument operating system and through the modem and modem data cable from the network.

10. The safety system of claim 9, further comprising:

an electrical power supply within the instrument coupled with an external power line that provides electrical power to the instrument operating system through an electrically isolated power transformer for blocking passage of hazardous electrical signals conducted through the external power line to the instrument operating system; and means for providing electrical power to the module operating system through the expansion bay interface connector including an electrically isolated power transformer that isolates the module operating system from hazardous electrical signals.

11. The safety system of claim 9, further comprising:

an analog signal cable interface connector coupled with the instrument operating system adapted to pass analog data to a remote instrument through an analog data transmission cable;

an elongated analog data transmission cable having a first end coupled with the analog signal cable interface connector and a second end coupled with a remote instrument; and analog signal interface circuitry including an opto-isolator for conducting analog signals between the analog signal cable interface connector and the instrument operating system and for blocking hazardous electrical signals passing through the analog data transmission cable from the remote instrument.

12. The safety system of claim 9, further comprising:

an ECG cable interface connector coupled with the instrument operating system adapted to be coupled with an ECG cable to pass ECG data to the instrument operating system;

an elongated ECG cable having a first end coupled with the ECG cable interface connector and a second end coupled with a plurality of ECG electrodes adapted to be applied to the skin of a patient's body; and ECG signal interface circuitry including an opto-isolator for conducting ECG analog signals between the ECG cable interface connector and the instrument operating system and for blocking the conduction of hazardous electrical signals through the ECG cable interface connector.

13. In an external medical instrument in physical contact with a patient's body to communicate with or test the function of implantable medical devices (IMDs) implanted in the patient's body or to measure a physiologic condition of the patient's body and capable of communicating with other medical instruments or systems located at a distance from the patient, a safety system for protecting the patient from harm due to hazardous electrical signals comprising:

an expansion bay of the external medical instrument adapted to receive a module expanding the capabilities of the external medical instrument, the expansion bay further comprising an expansion bay interface connector;

a module fitted into the expansion bay and connected with the expansion bay interface connector having a module operating system;

a cable coupling the module operating system with the patient's body for conducting electrical signals to and from the patients body;

a modem interface connector of the external medical instrument adapted to receive a modem;

a modem connected with the modem interface connector and with a data transmission network through a modem data cable, the modem adapted to transmit patient and IMD data to and from a remote location of a network;

an instrument operating system that creates and transmits module control data through the expansion bay interface connector in a transmission data path to the module operating system and receives module test data through the expansion bay interface connector in a reception data path from the module operating system and that creates and transmits patient and IMD data through the modem to the remote location; and an opto-isolator within the module and in the transmission data path and the reception data path for isolating the instrument operating system from the module operating system to block passage of hazardous electrical signals through the cable to the patient's body including hazardous signals conducted through the modem interface connector to the instrument operating system and through the modem and modem data cable from the network;

wherein the external medical instrument is an external programmer for receiving information-encoded, telemetry uplink signals transmitted from a IMD telemetry antenna and transmitter circuit in the IMD in a telemetry uplink transmission and for transmitting information-encoded telemetry downlink signals from a programmer telemetry antenna in a telemetry downlink transmission.

14. The safety system of claim 13, further comprising:

an electrical power supply within the instrument coupled with an external power line that provides electrical power to the instrument operating system through an electrically isolated power transformer for blocking passage of hazardous electrical signals conducted through the external power line to the instrument operating system; and means for providing electrical power to the module operating system through the expansion bay interface connector including an electrically isolated power transformer that isolates the module operating system from hazardous electrical signals.

15. The safety system of claim 13, further comprising:

an analog signal cable interface connector coupled with the instrument operating system adapted to pass analog data to a remote instrument through an analog data transmission cable;

an elongated analog data transmission cable having a first end coupled with the analog signal cable interface connector and a second end coupled with a remote instrument; and analog signal interface circuitry including an opto-isolator for conducting analog signals between the analog signal cable interface connector and the instrument operating system and for blocking hazardous electrical signals passing through the analog data transmission cable from the remote instrument.

16. The safety system of claim 13, further comprising:

an ECG cable interface connector coupled with the instrument operating system adapted to be coupled with an ECG cable to pass ECG data to the instrument operating system;

an elongated ECG cable having a first end coupled with the ECG cable interface connector and a second end coupled with a plurality of ECG electrodes adapted to be applied to the skin of a patient's body; and ECG signal interface circuitry including an opto-isolator for conducting ECG analog signals between the ECG cable interface connector and the instrument operating system and for blocking the conduction of hazardous electrical signals through the ECG cable interface connector.

17. In an external instrument adapted to be coupled with a patient's body to communicate with or test the function of implantable medical devices (IMDS) implanted in the patient's body or to measure a physiologic condition of the patient's body and capable of communicating with other medical instruments or systems located at a distance from the patient, a safety system for protecting the patient from harm due to hazardous electrical signals comprising:

a instrument operating system that processes and generates electrical signals;

a patient cable adapted to be coupled to a patient's body for transmitting electrical signals from the instrument operating system to the patient's body and for receiving electrical signals from the patient's body;

a data cable extending to a remote instrument or a network for communicating signals between the instrument operating system and the remote instrument or network;

first electrical isolation circuit means between the instrument operating system and the data cable for blocking conduction of hazardous electrical signals imposed upon the data cable from being conducted through the instrument operating system to the patient cable; and second electrical isolation circuit means between the patient cable and the instrument operating system for blocking conduction to the patient cable of hazardous signals conducted from the data cable through the instrument operating system.

18. The safety system of claim 17, wherein the external medical instrument is an external programmer for receiving information-encoded, telemetry uplink signals transmitted from a IMD telemetry antenna and transmitter circuit in the IMD in a telemetry uplink transmission and for transmitting information-encoded telemetry downlink signals from a programmer telemetry antenna in a telemetry downlink transmission.

* * * * *